United States Patent
Hood et al.

(10) Patent No.: US 6,537,214 B1
(45) Date of Patent: Mar. 25, 2003

(54) PATIENT MONITOR WITH CONFIGURABLE VOICE ALARM

(75) Inventors: Rush Hood, Tampa, FL (US); John Booth, Tampa, FL (US); Rick Medero, Tampa, FL (US)

(73) Assignee: GE Medical Systems Information Technologies, Inc., Milwaukee, WI (US)

( * ) Notice: Subject to any disclaimer, the term of this patent is extended or adjusted under 35 U.S.C. 154(b) by 0 days.

(21) Appl. No.: 09/951,081

(22) Filed: Sep. 13, 2001

(51) Int. Cl.[7] .................................................. A61B 5/00
(52) U.S. Cl. ...................... 600/300; 340/573.1; 600/485
(58) Field of Search ................................. 600/300, 301, 600/485; 340/573.1, 573.4, 460; 704/274; 607/32, 60

(56) References Cited

U.S. PATENT DOCUMENTS

| | | | |
|---|---|---|---|
| 5,494,046 A | * | 2/1996 | Cross ....................... 340/573.4 |
| 5,648,753 A | | 7/1997 | Martin |
| 6,048,310 A | * | 4/2000 | Yasushi et al. ............. 600/300 |
| 6,297,738 B1 | * | 10/2001 | Newham .................. 340/573.1 |
| 6,450,172 B1 | * | 9/2002 | Hartlaub et al. .............. 607/32 |

* cited by examiner

*Primary Examiner*—Eric F. Winakur
*Assistant Examiner*—David J. McCrosky
(74) *Attorney, Agent, or Firm*—George E. Haas; Quarles & Brady LLP

(57) ABSTRACT

A patient monitor has a plurality of voice alarm messages stored in a memory. When the monitor detects an occurrence of an alarm condition, such as an usual physiological characteristic of the patient, a voice alarm message associated with that condition is played back through a loudspeaker. To enable the patient monitor to be used throughout the world, the end user is able to replace each of the prerecorded voice alarm messages. Thus the end user is able to store voice messages in the native language and dialect spoken where the monitor is used.

18 Claims, 2 Drawing Sheets

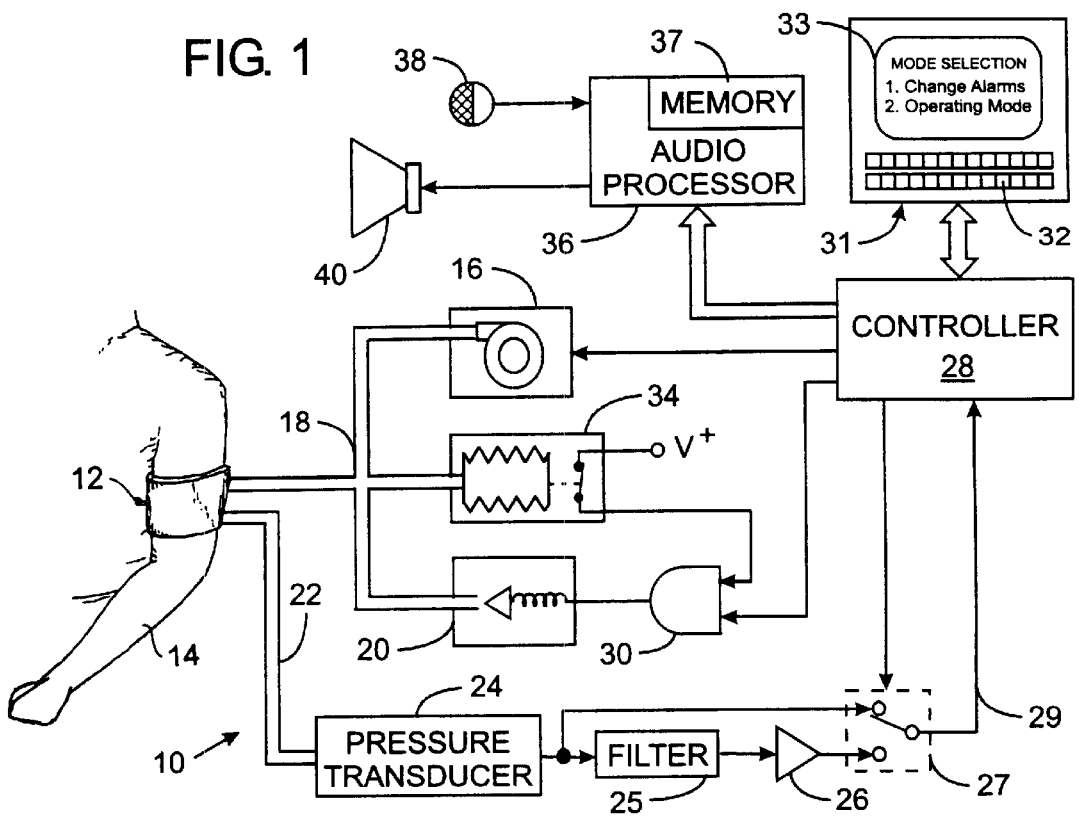

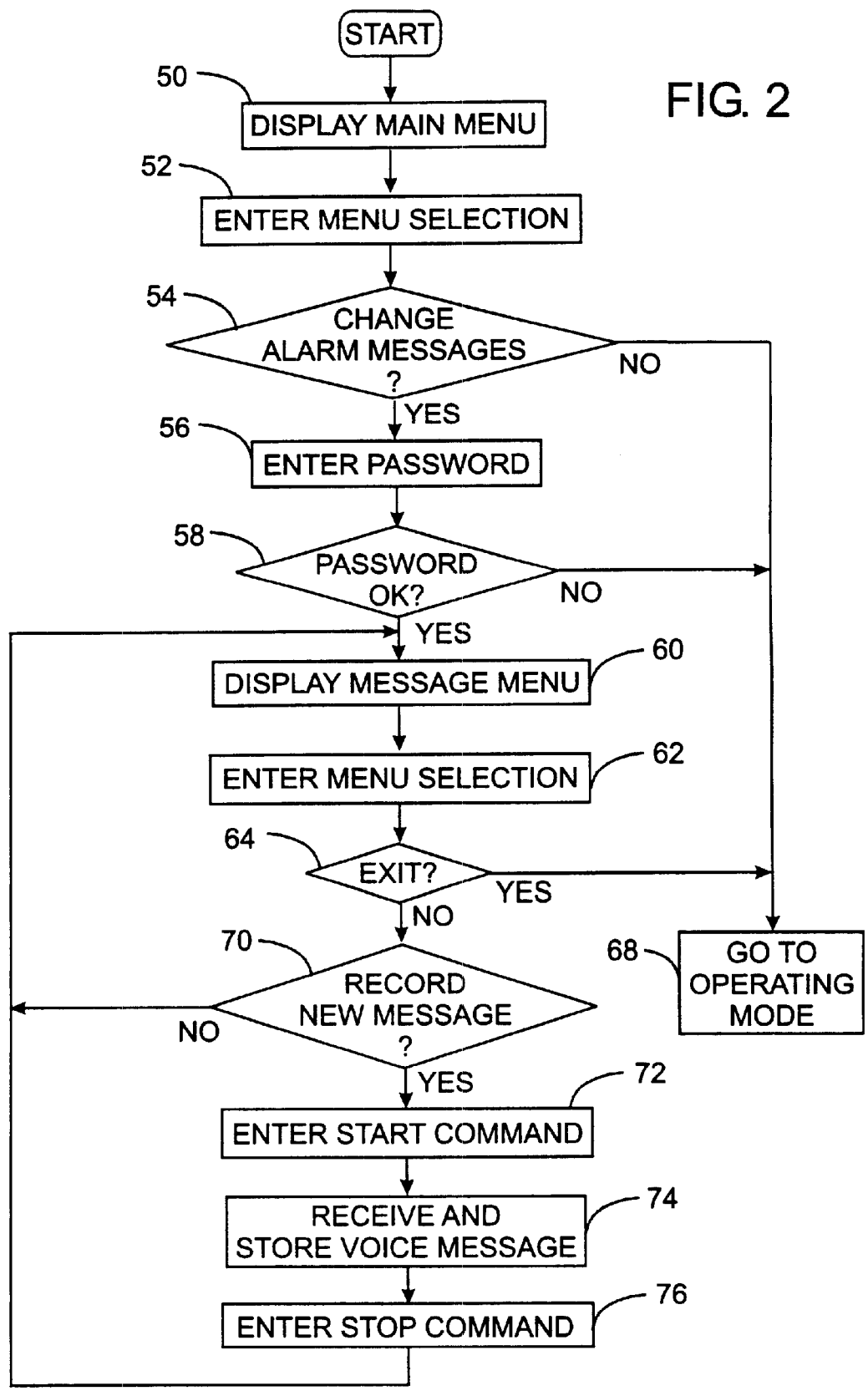

PATIENT MONITOR WITH CONFIGURABLE VOICE ALARM

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

The invention generally relates to apparatus for monitoring medical patients; and more particularly to such apparatus which include an audible alarm.

Medical patients, especially those in an intensive care facility, often are connected to equipment which continuously monitor specific physiological activity that is relevant to the particular malady of which the patient suffers. For example, a patient with heart disease may be connected to an electrocardiograph and a blood pressure monitor. Such monitors have sensors attached to the patient, analyze the signals from the sensors, and display the physiological information to the medical personnel. In the case of an electrocardiograph, the cardiac waveform is displayed on a graphical display device or printed out on paper. Blood pressure monitors will have numerical displays indicating the systolic pressure, diastolic pressure and possibly other parameters, such as mean arterial pressure.

Rather than requiring that medical personnel constantly monitor the display of physiological information, audible alarms are often provided in the event that the physiological parameters exceed reasonable limits for a particular patient. For example, the systolic and diastolic blood pressures can be compared to threshold values for each parameter. When a given threshold is exceeded, an audible alarm is activated in the monitor to alert the medical personnel. Indicator lights also are used to indicate an abnormal condition. Alarms also are provided to indicate a malfunction of the monitoring equipment, such as a low battery charge for portable equipment or the sensor signal being lost as occurs when the sensor detaches from the patient.

Such audible alarms typically produce a relatively loud piercing sound so as to be heard over other sounds in the area of monitoring. As a consequence, the audible alarms may agitate the patient which in certain medical conditions is very undesirable. Furthermore, the patient may be agitated unnecessarily when the alarm indicates a relatively non-critical event, such as a loose sensor lead.

Furthermore, the use of an audible alarm such as produced by a piezoelectric annunciator or buzzer does not provide an indication of the exact condition for which the alarm is being sounded. The same annunciator may be used to indicate a number of events, such as the physiological parameters going out of bounds, a low battery, or a loose electrical sensor. However, the medical personnel cannot determine the nature of the alarm condition from the sound and thus, cannot determine whether an immediate response is required or whether the alarm condition can be remotely deactivated, such as from a nurse's station.

It has been proposed to provide a warning mechanism which produces a stored voice message indicating the nature of the alarm condition and even providing a message to soothe the patient to prevent agitation during this event. However, in order for medical equipment to be marketable worldwide, the alarm messages must be presented in the native language of the country in which the equipment will be used. If the medical personnel will not understand a message recorded in another language, then the alarm feature is useless. This leads to a requirement that the given medical monitor must be produced with a model for different languages and various dialects. This is especially unfeasible in the case of a relatively small nation with a unique language. Furthermore, different applications of a monitor in hospitals, clinics, or home settings may call for different message phrases for the same conditions. Different medical facilities using the same language also may refer to a given Medical event by different phrases.

Thus there is a need to be able to easily customize a patient monitor's voice messaging system for the particular location at which it is being used.

BRIEF SUMMARY OF THE INVENTION

A patient monitor has one or more audio messages stored in a memory. When the patient monitor detects an occurrence of a predefined condition, such as an usual physiological characteristic of the patient, an audio message associated with that condition is played back through a loudspeaker. To enable the patient monitor to be used throughout the world, the end user is able to replace each prerecorded audio message. Thus the end user is able to store voice messages in the native language and dialect spoken where the monitor is used.

Specifically, the patient monitor incorporating the audio messaging system has circuitry which senses a physiological characteristic of a medical patient and produces a control signal indicating an occurrence of a predefined event. An audio input device, such as a microphone for example, and a loudspeaker are provided. An audio processor has an input connected to the audio input device and has an output connected to the loudspeaker. A control input is coupled to the circuitry for receiving the control signal. A memory is included to store an audio message related to the event. The audio processor has a first operating mode in which a signal produced by the user is received at the input and stored in the memory as the audio message. In a second operating mode of the audio processor responds to receipt of the control signal by retrieving the stored audio message from the memory and generating a signal at the output.

DESCRIPTION OF THE OF THE DRAWINGS

FIG. 1 is a block diagram of an apparatus for monitoring blood pressure of a medical patient; and FIG. 2 is a flowchart of a process for configuring the apparatus with voice messages to be emitted upon an occurrence of an alarm condition associated with each message.

DETAILED DESCRIPTION OF THE INVENTION

The present invention will be described in the context of an automatic blood pressure measuring apparatus. However it is understood that the invention can be applied to a wide variety of types of patient monitors in which an alarm is desired to alert medical personnel. For example the apparatus may detect other physiological characteristics of a medical patient such as temperature, oxygen saturation level of blood, cardiac activity, or brain activity.

With reference to FIG. 1, an automatic blood pressure monitor 10 employs an inflatable cuff 12 shown wrapped around an arm 14 of a medical patient. The inflatable cuff 12 is connected to a pump 16 by a flexible first tube 18. The first tube also connects to an electrically operated deflation valve 20 and to a protective over pressure switch 34 which responds to excessive pressure being applied to the cuff 12. A flexible second tube 22 couples the cuff 12 to a pressure transducer 24 which produces an electrical signal at output that indicates the pressure within the cuff.

The pressure transducer output is coupled to a band pass filter 25 which in turn is connected to an amplifier 26. The filter 25 and amplifier 26 are designed to reject the d.c. component of pressure signal produced by the transducer 24 and yet amplify the blood pressure oscillations, as will be described. Specifically, the band pass filter 25 passes those signals having frequency components in a range from one to ten Hertz and strongly rejects other frequency components. The amplifier 26 magnifies low level signals from the filter 25. The output signal from the amplifier 26 corresponds to the oscillations, or the a.c. component, of the pressure in the cuff 12. This filters out the component of the transducer signal due to the inflation pressure of the cuff. The pressure sensing apparatus and method has been used in previous blood pressure monitors and are well known to those skilled in the art.

The output of the amplifier 26 is connected to one input of a multiplexer 27 which has another input to which the output of the pressure transducer 24 is directly connected. The multiplexer 27 selects one of the two input signals which is coupled to an analog input 29 of a controller 28 that governs the operation of the blood pressure monitor 10.

The controller 28 is a computerized device which includes a conventional microprocessor and a memory which stores the software program that controls operation of the blood pressure monitor 10 and stores data used in the execution of that program. Input and output circuits interface the controller 28 to other components of the blood pressure monitor. For example, an input/output port is provided for an operator interface 31 comprising a control panel 32, with a plurality of pushbutton switches, and a display device 33, such as a liquid crystal display or a cathode ray tube monitor. In addition, the output of the multiplexer 27 is connected to an input of an analog to digital converter within the controller 28. A controller output is connected to operate the cuff inflation pump 16.

Another output of the controller 28 is coupled to a one input of an AND gate 30. The AND gate 30 has another input connected to the overpressure switch 34 and has an output that is connected to control the deflation valve 20. In the event of an excessive pressure in the cuff 12, the overpressure switch 34 opens resulting in the output of the AND gate opening the deflation valve 20 to relieve that excessive cuff pressure.

The blood pressure monitor 10 also includes an audio processor 36 which may be any of a number of commercially available voice recording and playback integrated circuits. For example, the audio processor 36 may be a model ML2500BTA Analog-Storage Single-chip Record/Playback LSI manufactured by Oki Semiconductor, Sunnyvale, Calif. U.S.A. The audio processor 36 has an audio input connected to a microphone 38 and an audio output to which a loudspeaker 40 is connected. As used herein, the term "microphone" refers to any device that converts and acoustical signal into an electrical signal, and the term "loudspeaker" refers to any device that converts an electrical signal into an acoustical signal. The audio processor 36 has an internal random access memory 37 for storage of a plurality of voice messages which are individually addressable by the controller 28, as will be described. As such the audio processor 36 has address and control pins connected to the controller 28. Unlike prior speech synthesis modules for patient monitors, the message storage locations can be programmed by the user with the desired message in a particular language that is understood by the attending medical personnel.

When the blood pressure monitor 10 is assembled, the manufacturer programs the audio processor 36 with a set of default alarm messages in a particular language, English, for example. The end user of the monitor has the option of using the default messages or changing the messages either into another language or to other phrases that identify each alarm condition. The ability to change the configuration of the messages stored in the audio processor 36 is presented to the user upon initial power-up of the blood pressure monitor 10. At that time, the controller 28 begins executing a software program, the initial steps of which are depicted in FIG. 2. At step 50, the controller 28 transmits information to the display device 33 so that a main menu of operating modes is displayed to the user. One of these modes relates to changing the alarm messages. The program execution waits at step 52 for the user to enter a menu selection onto the control panel which then is interpreted by the controller at step 54 to determine whether the user has selected the change alarm message mode. If another mode is selected process branches to step 68 to go to the operating mode.

When the user desires to change the alarm messages, the program execution branches from step 54 to step 56, where the user is asked to enter a password into the control panel 33, which prevents unauthorized personnel from changing the alarms messages. The entry then is authenticated at step 58 before proceeding further in this mode.

When access to change the messages has been granted, the procedure advances to step 60 at which another menu containing a list of the various messages that can be programmed is shown on the display device 33. The user is able to refer to the operating manual for the blood pressure monitor 10 to determine the default text of each of the alarm messages which has been programmed by the manufacturer. Then the control panel is employed to select one of the menu choices at step 62 and a determination is made at step 64 whether the user chose to exit the message changing mode. If that is not the case, process advances to step 70.

At step 70, the user is asked, via a question presented on the display device 33, whether the message for the selected alarm is to be changed. If so, the user is prompted at step 72 to press a button on the control panel 32 to start recording the new message. Thereafter at step 74, the audio processor 36 begins digitizing and storing the audio signal from the microphone 38. The digitized audio message is stored in the processor's memory 37 at a location assigned to the associated alarm condition. Thus, the user is able to customize each of the alarm messages to the native language of the country in which the equipment will be used, as well as into a particular dialect. The user is also afforded the opportunity to change the text of the message even though the language may not vary. Upon the completion of speaking the text of the new message, the user activates another button on the control panel 32 which signals the controller to terminate message recording at step 76.

The procedure then returns to step 60 where the user is prompted to select another item from the message change menu.

After configuration of the alarm messages, the blood pressure monitor is placed into service. The measurement of a patient's blood pressure is similar to that described in U.S. Pat. No. 4,360,029, the description of which is incorporated herein by reference.

In summary, the cuff 2 is wrapped around the arm 14 of a patient and the attendant then activates a switch on the control panel 32 which commences the measurement operation. Periodically, the controller 28 produces output signals which close the deflation valve 20 and activate the pump 16 to inflate the cuff 12. As the cuff is being inflated, the controller monitors the electrical signal from the pressure transducer 24 which indicates the pressure within the cuff 12. The cuff is inflated to a predefined pressure which is known to occlude the flow of blood within the blood vessels of the arm 14. Once this occlude pressure has been obtained, the controller 28 terminates operation of the pump 16 while maintaining the deflation valve 20 in a closed state.

The controller 28 then begins a controlled deflation of the cuff 12 while periodically measuring the pressure therein. In the preferred embodiment of the present invention, the controller gradually deflates the cuff in a series of steps and the nominal pressure at each step is referred to herein as the "deflation step pressure".

The instantaneous pressure at each step does not always equal the deflation step pressure, but oscillates slightly due to the force exerted on the cuff 12 by the blood pulsing through the patient's blood vessels. A plurality of pressure measurements are taken at each step to measure those pressure oscillations. At this time the controller 28 applies a signal to the multiplexer 27 which responds by connecting the output from the amplifier 26 to the controller's analog input 29. Thus the controller receives a signal which corresponds to the blood pressure oscillations about the deflation step pressure in the cuff 12. This signal is digitized by the controller circuits and the signal samples is stored in memory as an oscillation pressure measurement. After a predefined number of such measurements has been taken, the cuff is deflated to the next deflation step pressure and another set of measurements is acquired.

When the cuff 12 has been fully deflated, the controller 28 commences analyzing the plurality of pressure oscillation measurements to determine the mean arterial pressure, the systolic pressure and the diastolic pressure of the patient using conventional techniques. Each of these values is compared to a corresponding threshold. An alarm condition exists when one of the thresholds is exceeded. In that event the controller 28 sends a playback command and the address of the message to the audio processor 36. The audio processor 36 responds to those signals by accessing the corresponding digitized voice message in internal memory 37 and using that data to send an audio signal to the loudspeaker 40.

The foregoing description was primarily directed to a preferred embodiment of the invention. Although some attention was given to various alternatives within the scope of the invention, it is anticipated that one skilled in the art will likely realize additional alternatives that are now apparent from disclosure of embodiments of the invention. Accordingly, the scope of the invention should be determined from the following claims and not limited by the above disclosure.

What is claimed is:

1. A medical patient monitor having an audio messaging system, the medical patient monitor comprising:
    a circuit which measures a physiological characteristic of a medical patient and produces a control signal in response to the physiological characteristic having a defined measured value;
    an audio input device;
    a loudspeaker; and
    an audio processor having an input connected to the audio input device, an output electrically connected to the loudspeaker, a control input connected to the circuit for receiving the control signal, and a memory for storing an audio message related to the predefined event, the audio processor having a first mode in which a first signal received at the audio input is stored in the memory, and having a second mode in which the first signal is retrieved from the memory and used to generate a signal at the output in response to receiving the control signal.

2. The medical patient monitor as recited in claim 1 wherein the audio input device comprises a microphone.

3. The medical patient monitor as recited in claim 1 further comprising an operator interface connected to the circuit and comprising a control panel and a display device.

4. The medical patient monitor recited in claim 1 further comprising a control panel coupled to the audio processor and by which a user of the medical patient monitor selects between the first and second modes.

5. The medical patient monitor as recited in claim 4 wherein the control panel comprises a user input device to initiate storing the first signal in the memory.

6. The medical patient monitor as recited in claim 4 wherein the control panel comprises a user input device to terminate storing the first signal in the memory.

7. The medical patient monitor as recited in claim 1 further including a mechanism that enables the audio processor to operate the first mode only in response to entry of a security code by a user.

8. The medical patient monitor as recited in claim 1 wherein the physiological characteristic is selected from a group consisting of blood pressure, temperature, blood oxygen saturation, cardiac activity, and brain activity.

9. An audio messaging system for a medical monitor that measures a physiological characteristic of a medical patient and produces control signals in response to the physiological characteristic having different defined measured values, the audio messaging system comprising:
    an audio input device;
    a loudspeaker; and
    an audio processor having an input connected to the audio input device, an output electrically connected to the loudspeaker, a control input for receiving the control signals and a memory which stores a plurality of prerecorded messages each of which is related to one of the different defined measured values, the audio processor having a first mode in which a user replaces at least one of the plurality of prerecorded messages with an audio signal received from the audio input device, and having a second mode which a message is retrieved from the memory and used to generate a signal at the output in response to receiving a particular one of the control signals from the patient monitor.

10. The audio messaging system as recited in claim 9 wherein the audio input device comprises a microphone.

11. The audio messaging system as recited in claim 9 further comprising an operator interface coupled to the audio processor and comprising a control panel and a display device.

12. The audio messaging system as recited in claim 9 further comprising a control panel by which a user of the medical patient monitor selects between the first and second modes.

13. The audio messaging system as recited in claim 12 wherein the control panel provides a mechanism by which the user selects one of the plurality of prerecorded messages to be replaced.

14. A method of producing alarm messages from a medical monitor that measures a physiological characteristic of a patient, said method comprising steps of:

(a) a user of the medical monitor speaking an alarm message into a microphone that is connected to the medical monitor;

(b) recording the alarm message in a memory connected to the medical monitor;

(c) generating a control signal in response to the physiological characteristic having a defined measured value;

(d) in response to the control signal, retrieving the alarm message from the memory; and (e) employing the retrieved alarm message to generate a signal that is applied to a loudspeaker that is electrically connected to the medical monitor.

15. The method as recited in claim 14 which further comprises entering a password; determining whether the password is valid by a comparison to a database of valid passwords; and if the password is valid then enabling recording the alarm message.

16. The method as recited in claim 15 further comprising identifying a location in the memory at which a particular alarm message is to be recorded.

17. The method as recited in claim 15 wherein receiving a control signal comprises receiving an identification of one of the plurality of alarm messages to be retrieved from the memory.

18. The method as recited in claim 14 further comprising repeating steps (a) and (b) to record a plurality of alarm messages.

* * * * *